(12) United States Patent
Carroll et al.

(10) Patent No.: US 7,228,178 B2
(45) Date of Patent: Jun. 5, 2007

(54) SURFACE STIMULATION FOR TREMOR CONTROL

(75) Inventors: William J. Carroll, La Center, WA (US); Richard M. Terrell, Vancouver, WA (US)

(73) Assignee: International Rehabilitative Sciences, Inc., Vancouver, MA (US)

( * ) Notice: Subject to any disclaimer, the term of this patent is extended or adjusted under 35 U.S.C. 154(b) by 336 days.

(21) Appl. No.: 10/717,925

(22) Filed: Nov. 21, 2003

(65) Prior Publication Data

US 2004/0138722 A1    Jul. 15, 2004

Related U.S. Application Data

(60) Provisional application No. 60/428,281, filed on Nov. 22, 2002.

(51) Int. Cl.
*A61N 1/00* (2006.01)
(52) U.S. Cl. ............................................. 607/45
(58) Field of Classification Search ............... 607/45, 607/72
See application file for complete search history.

(56) References Cited

U.S. PATENT DOCUMENTS

| | | | | |
|---|---|---|---|---|
| 6,161,044 A * | 12/2000 | Silverstone | ............... | 607/45 |
| 6,594,524 B2 * | 7/2003 | Esteller et al. | ............... | 607/45 |
| 6,647,296 B2 | 11/2003 | Fischell et al. | | |
| 6,937,905 B2 * | 8/2005 | Carroll et al. | ............... | 607/51 |
| 2002/0169485 A1 * | 11/2002 | Pless et al. | ............... | 607/48 |

OTHER PUBLICATIONS

Mohamed A. Hamza, M.D., et al., Effect of the Duration of Electrical Stimulation on the Analgesic Response in Patients with Low Back Pain, Anesthesiology, Dec. 1999, pp. 1622-1627, vol. 91, No. 6.
El-Sayed A. Ghoname, M.D., et al., The Effect of Stimulus Frequency on the Analgesic Response to Percutaneous Electrical Nerve Stimulation in Patients with Chronic Low Back Pain, Anesthesia & Analgesia, Apr. 1999, pp. 841-846, vol. 88, No. 4.
Richard E. Seroussi, MD, et al., Effectiveness of Percutaneous Neuromodulation Therapy for Patients with Chronic and Severe Low Back Pain, 2003, pp. 22-30, vol. 3, Issue 1, Pain Practice.
El-Sayed A. Choname, MD, et al., Percutaneous Electrical Nerve Stimulation for Low Back Pain, JAMA, Mar. 3, 1999, vol. 281, No. 9.
Andrew J. Robinson, Clinical Electrophysiology, Electrotherapy and Electrophysiologic Testing, pp. cover, 285, 288-290, Second Edition, Williams & Wilkins.

(Continued)

*Primary Examiner*—Scott M. Getzow
(74) *Attorney, Agent, or Firm*—Blank Rome LLP.

(57) ABSTRACT

Apparatus and methods for non-invasive electrical stimulation of the brain through skin surface stimulation of the peripheral nervous system as a treatment for movement disorders. Skin surface electrodes are positioned at predetermined peripheral surface stimulation sites on the skin surface using a variety of neural imaging techniques. A pulsatile electrical current is generated at the stimulation sites through a variety of standard electrical stimulation devices. Stimulation of the peripheral surface stimulation sites translates to electrical stimulation of a specific area of the brain.

30 Claims, 2 Drawing Sheets

OTHER PUBLICATIONS

M.I. Johnson, et al., An in-depth study of long-term users of transcutaneous electrical nerve stimulation (TENS). Implications for clinical use of TENS, Pain 41, 1991, pp. 221-229, Elsevier Science Publishers B.V.

J.S. Han, et al., Effect ov low- and high-frequency TENS on Met-enkephalin-Arg-Phe and dynorphin A immunoreactivity in human lumbar CSF, 1991, pp. 295-298, Elsevier Science Publishers B.V.

Roger M. Nelson, et al., Clinical Electrotherapy, third edition, Appleton & Lange, Stamford, Connecticut.

Vertis Percutaneous Neuromodulation Therapy (PNT), Peer Review Network, Inc., PRN Newsletter, Nov. 2002, vol. 9, No. 6., pp. 1-5.

Priya Gopalkrishnan, MS, et al., Effect of Varying Frequency, Intensity, and Pulse Duration of Transcutaneous Electrical Nerve Stimulation on Primary Hyperalgesia in Inflamed Rats, Arch Phys Med Rehabil, vol. 81, Jul. 2000, pp. 984-990.

M.I. Johnson, et al., Analgesic effects of different frequencies of transcutaneous electrical nerve stimulation on cold-induced pain in normal subjects, Pain 39 (1989), pp. 231-236, Elsevier Science Publishers B.V.

Serge Marchand, M.Sc., et al., Modulation of Heat Pain Perception by High Frequency Transcutaneous Electrical Nerve Stimulation (TENS), The Clinical Journal of Pain, vol. 7, No. 2, 1991, pp. 122-129.

PCT/US03/37372 International Search Report, Nov. 21, 2003, International Rehabilitative Sciences, Inc.

Katayama Y., Deep brain stimulation therapy for involuntary movements, Rinsho Shinkeigaku, Dec. 1, 2001 00:00; 41(12):1079-80, 1 page.

Benabid Al, et al., Deep btrain stimulation of the corpus luysi (subthalamic nucleus) and other targets in Parkinson's disease. Extension to new indications such as dystonia and epilepsy, J. Neurol. Sep. 1, 2001 00:00; 248 Suppl 3:III37-47, 2 pages.

Allert N., et al., Effects of bilateral pallidal or subthalamic stimulation on gait in advanced Parkinson's disease, Mov Disord. Nov. 1, 2001 00:00; 16(6):1076-85, 2 pages.

Utti RJ, et al., Extended Follow-up of Unilateral Deep Brain Stimulation for Tremor, Deep brain stimulation remains an effective treatment for tremor for at least 3 years, according to this article, P03.1123; A220-221.

Obwegeser AA, et al., Quantitative and qualitative outcome measures after thalamic deep brain stimulation to treat disabling tremors, Neurosurgery, 48(2): 274-81, discussion 281-4 2001, 2-page Article.

Obwegeser AA, et al., Simultaneous thalamic deep brain stimulation and implanatable cardioverter-defibrillator, Mayo Clin Proc, 76(1): 87-9, 2001, 2-page Abstract.

Obwegeser AA, et al., Thalamic stimulation for the treatment of midline tremors in essential tremor patients, Nekurology, 54(12): 2342-4 2000, 2-page Abstract.

Oh My, et al., Deep brain stimulator electrodes used for lesioning: proof of principle, Neurosurgery, Aug. 1, 2001 00:00; 49(2): 363-7; discussion 367-9, 2-page Article.

Racette BA, et al., Thalamic stimulation for primary writing tremor, J Neurol. May 1, 2001 00:00; 248(5): 380-2, 2-page Report.

Rocchi L, et al, Effects of deep brain stimulation and levodopa on postural sway in Parkinson's disease, J. Neuro Neurosurg Psychiatry, Sep. 2002; 73(3):267-74, 2-page Article.

Nasser JA, et al, Deep brain stimulation of VIM Thalamic nucleus for tremor control, Arq Neuropsiquiatr. Jun. 2002; 60(2-B):429-34, 1-page Article.

Racette BA, et al., Ipsilateral thalamic stimulation after thalamotomy for essential tremor. A case report., Stereotact Funct Neurosurg. Jan. 1, 2000 00:00; 75(4): 155-9, 2-page Article.

Rerzai AR, et al., Neurostimulation systems for deep brain stimulation: in vitro evaluation of magnetic resonance imaging-related heating at 1.5 tesla, J Magn Reson Imaging, Mar. 1, 2002 00:00; 15(3):241-50, 2-page Article.

Maya Pines, New Imaging Techniques That Show the Brain at Work: Brain Scans That Spy on the Senses, Seeing, Hearing, and Smelling the World, A Report from the Howard Hughes Medical Institute, 2-page Article.

Maya Pines, New Imaging Techniques That Show the Brain at Work: The Next Generation of Brain Scans, Seeing, Hearing, and Smelling the World, A Report from the Howard Hughes Medical Institute, 2-page Article.

Oregon Imaging Article, P.E.T. Scan—Patient Information, 2 page Article.

Cigna Corporation, Positron Emission Tomography (PET) Scans—Medical Coverage, All States, 1999, 7-page Article.

Rezai AR, et al., Neurostimulation systems for deep brain stimulation: In vitro evaluation of magnetic resonance imaging-related heating at 1.5 tesla, J magn Reson Imaging, Mar. 1, 2002 00:00; 15(3):241-50, 2-page Article.

Mobile Pet Systems, Inc., Clinical Applications, 5-pages.

Neurological Associates, Inc., Deep Brain Stimulation, West Virginia, 6-page Article.

\* cited by examiner

SURFACE STIMULATION FOR TREMOR CONTROL

The present application claims priority to Provisional Patent Application No. 60/428,281, filed Nov. 22, 2002, whose disclosure is hereby incorporated by reference in its entirety into the present disclosure.

FIELD OF THE INVENTION

The present invention is generally related to tremor control, and more particularly, is related to an apparatus and methods for the electrical stimulation of the brain through skin surface stimulation of the peripheral nervous system for the treatment of movement disorders.

BACKGROUND OF THE INVENTION

In the last decade, the use of deep brain stimulation (DBS) has demonstrated dramatic improvement in symptoms associated with movement disorders, including symptoms from Parkinson's disease (PD), Essential Tremor (ET) and dystonia.

Essential Tremor is an involuntary movement, such as a shaking movement that is repeated over and over. Essential Tremor usually affects the hands and head, although occasionally the feet or torso may also be affected. Essential tremor, which sometimes runs in families, is one of the most common types of tremor. It causes shaking that is most noticeable when a person is performing a task like lifting a cup or pointing at an object. The shaking does not occur when the person is not moving. The tremor may also affect the person's voice. Medication can help reduce the shaking. Tremors can also be caused by conditions or medications that affect the nervous system, including Parkinson's disease, liver failure, alcoholism, mercury or arsenic poisoning, lithium, and certain antidepressants.

Instead of destroying the overactive cells that cause symptoms from PD, for example, DBS instead temporarily disables the cells by firing rapid pulses of electricity between four electrodes at the tip of a lead. The lead is permanently implanted and connected to a pacemaker controller installed beneath the skin of the chest.

DBS utilizes electrodes that are usually implanted in one of three regions of the brain: the thalamic nucleus ventral is intermedius (Vim), the internal globus pallidus (GPi), and the subthalamic nucleus (STN) (FIG. 1). Some studies have shown that DBS has the best effect on tremors, when the Vim is stimulated. Rigidity and gait disturbances have shown improvements with stimulation of GPi and STN. The parameters of 130-185 Hz, 60 ms pulse width and 2.5 to 3.5 volts are most commonly utilized for DBS stimulation. DBS stimulation is typically pulsed intermittent stimulation having an on cycle of about a few seconds up to a minute, then an off cycle for about 30 seconds to several minutes.

The challenge of DBS is the obvious drawback of having to undergo a neuro-surgical procedure and also to have the result of one or two electrodes implanted deep within the structures of the brain.

The present invention achieves tremor control through brain stimulation without the use of the invasive DBS electrodes. Stimulation of peripheral nerves results in the excitation of some area of the brain (Thalmus, sub-cortical and Cortical areas). The stimulation of sites on the surface of the skin produces effects of tremor control which are similar to the effects achieved by DBS for limited amounts of time. Surface stimulation is achieved through the use of surface electrodes that are currently used for Muscle Stimulation or TENS. Following a 30-60 minute stimulation time, there is a residual decrease in tremor of at least 30-60 minutes. The device can be worn under the clothing and activated while the decreased tremor period is desired.

PET (Positron Emission Tomography) scans, a molecular medical imaging procedure that uses small amounts of radioactive pharmaceuticals to make images of the body's metabolic activity, Magnetoencephalography (MEG) scans and fMRI scans can be used to identify appropriate peripheral surface stimulation sites. Various types of stimulation can be used including TENS, Neuro-Muscular Stimulation, Ultra Sound, Interferential Stimulation, PEMF, EMF, and various types of mechanical stimulation.

Thus, a heretofore unaddressed need exists in the industry to address the aforementioned deficiencies and inadequacies associated with a neuro-surgical procedure and the implantation of at least one electrode deep within the structures of the brain.

SUMMARY OF THE INVENTION

Embodiments of the present invention provide an apparatus and methods for surface electrical stimulation of the peripheral nervous system at predetermined peripheral stimulation sites for the treatment of movement disorders.

In a preferred embodiment, the peripheral stimulation sites, which are linked to specific areas of the brain, are initially traced using dermatome maps and then verified using PET scans, MEG scans, fMRI or other neural imaging devices. The electrical stimulator may utilize an interferential current that has a base medium frequency alternating current between 1 KHz and 100 KHz. An interferential current is set up between two circuits that are arranged in a cross-pattern on the subject's targeted area of stimulation. Where the circuits superimpose in a cross-pattern, the resultant beat frequency will be the difference between the frequencies of the two circuits and will usually range between 0-250 Hz and can be dynamic, and the amplitude will be additive and greater than either circuit alone.

Digital signal processors (DSPs) are used for improving the accuracy and reliability of digital signals that are used extensively in the communications field. Digital signal processing works by standardizing or clarifying the output of a digital signal. In this embodiment, the digital signal processor is used to shape multiple pulsatile waveforms to approximate the output of a sine-wave generator. In another embodiment of the invention, the digital signal processor is replaced with a field-programmable gate array (FPGA). A FPGA is an integrated circuit that can be programmed in the field after it is manufactured and therefore allows users to adjust the circuit output as the needs change. Both the DSP and the FPGA process a digital signal into a pseudo-sine-wave current waveform from the digital pulses generated by a pulse generator. The pseudo-sine-wave current waveform is transmitted through surface electrodes at a targeted area creating an interferential current.

The electrical stimulator may also use a standard TENS or NeuroMuscular stimulation waveform. Such devices produce a pulsatile current with a square wave output, an amplitude range from 0-150 mA and a phase duration (pulse width) range of 1-500 μsec. The frequency of such devices can range from 1 pulse per second (pps) to 2500 pps. The devices can be set to various duty cycles (on and off times) from as little as 1 second to 30 minutes on, and an off time as little as 1 second to as long as several minutes. The device can also be set to a continuous output without a duty cycle.

The device may utilize as little as one pair of electrodes, or multiple sets may be more effective depending on the condition of the patient.

Once identified, the peripheral stimulation sites are stimulated with the surface electrical stimulation device.

Other systems methods, features and advantages of the present invention will be or become apparent to one skilled in the art upon examination of the following drawings and detailed description. It is intended that all such additional systems, methods, features and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENTS

A preferred embodiment of the invention and modifications thereof will now be described with reference to the drawings.

Figure 1:
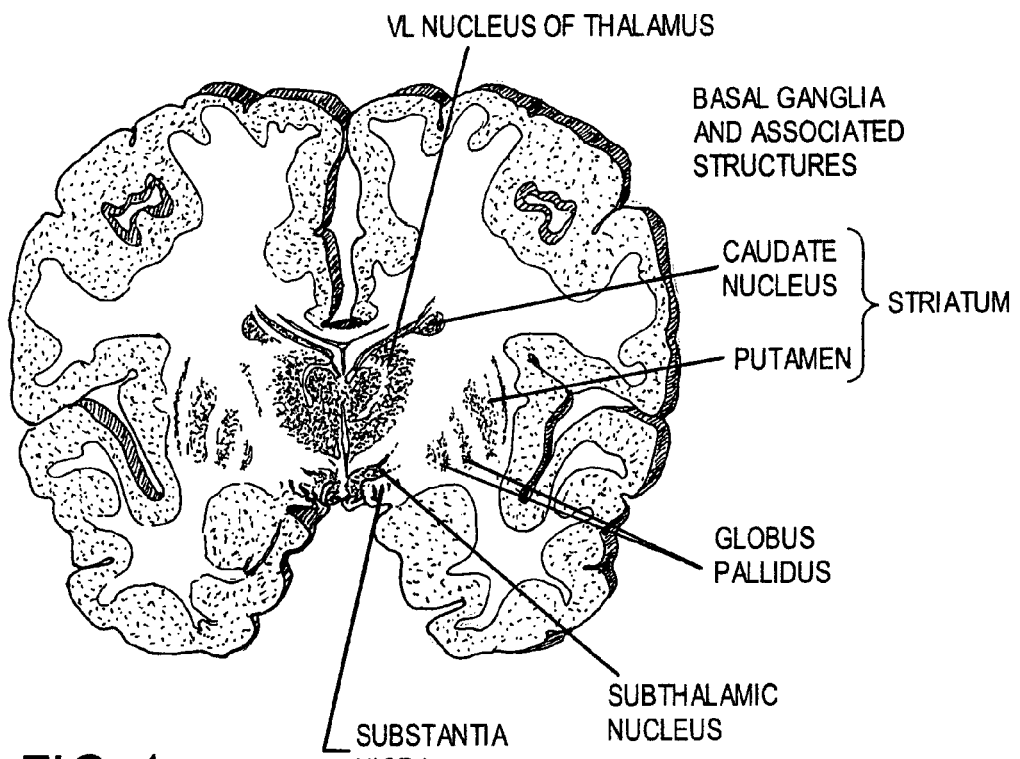
FIG. 1 is a drawing of the potential stimulation sites in the brain for deep brain stimulation for movement disorders.
Figure 4:
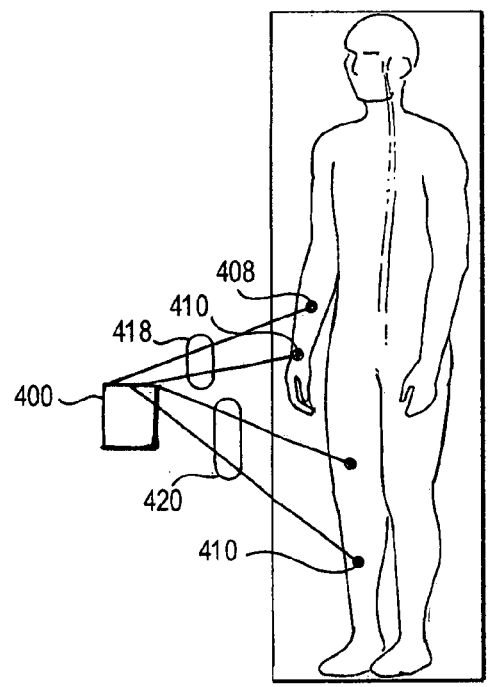
FIG. 4 is a drawing of a stimulator with surface electrodes positioned at peripheral stimulation sites.

FIG. 1 shows the potential stimulation sites in the brain for deep brain stimulation via surface stimulation of the peripheral nervous system. Using dermatome maps (not shown) of the peripheral nervous system, which can then be confirmed by PET scans (not shown) of the brain, peripheral surface stimulation sites 410 on a subject's skin surface are determined (FIG. 4). The stimulation of the peripheral surface stimulation sites 410 on the surface of the skin produces effects of tremor control which are similar to the effects achieved by DBS for limited amounts of time. The excited peripheral nerves would in turn excite similar, but not necessarily, the same areas of the brain that are currently stimulated by DBS.

Figure 2:
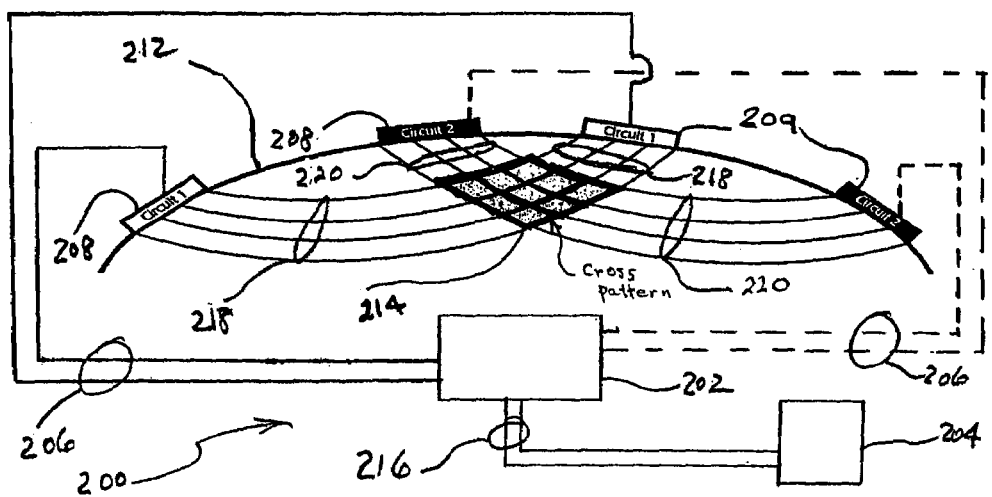
FIG. 2 is a drawing of a perspective view of an interferential current set up by two circuits.

FIG. 2 shows a stimulator 200 for the electrical stimulation of the peripheral nerves for tremor control at the peripheral surface stimulation sites utilizing an interferential current 210 that has a base medium frequency alternating current between 1K-100 KHz. Such a stimulator 200 is shown, for example, in U.S. Pat. No. 6,393,328, issued on May 21, 2002 to the assignee of the present application. Other TENS, Neuromuscular stimulation devices, Ultrasound, Pulsed Electromagnetic Field generators, EMF generators and mechanical stimulation devices can also be utilized (not shown).

The interferential current 210 is set up between two circuits 218, 220, 418, 420 that are arranged in a crosspattern. A first pair of surface electrodes 208, 209 are positioned on a subject's skin surface at the peripheral surface stimulation site 410 on one set of diagonal corners of a targeted area 114, 314 (see FIG. 3). The targeted area is the peripheral nerve and surrounding area to be stimulated. A second pair of surface electrodes 209, 309, and 408, is then positioned at the other set of diagonal corners of the targeted area 114, 314. A digital signal processor 202 is connected to the first and second pairs of surface electrodes 208,209; 308,309; and 408. When a signal-generating source 204 is connected to the digital signal processor 202, a sine-wave-like waveform signal output 206 is created. The digital signal processor 202 improves the accuracy and reliability of the digital signals. The digital signal processor 202 processes the multiple pulses from the signal generating source 204 to approximate a sine-wave (pseudo-sine-wave or sine-wave-like). The digital signal processor 202 generates individual pulses 206 of differing widths and resultant amplitudes. When those differing pulses 206 are driven into a transformer (not shown), the pseudo-sine-wave is produced.

Figure 3:
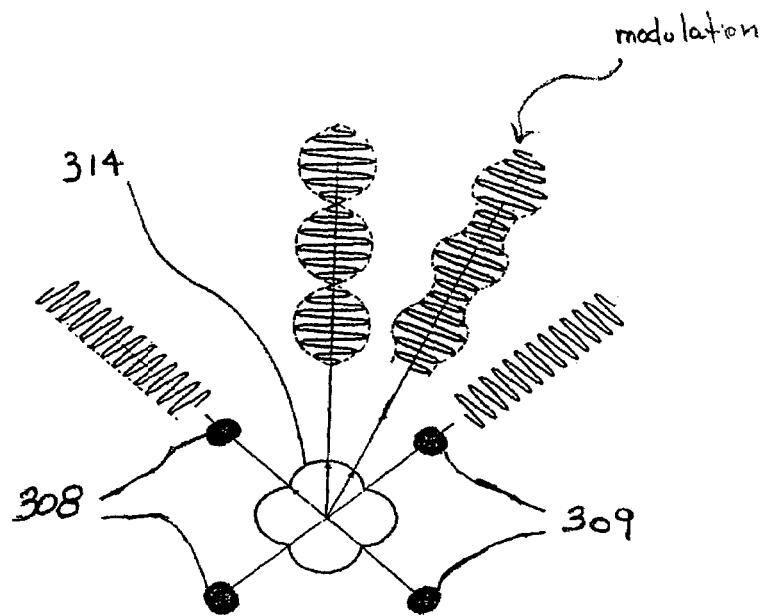
FIG. 3 is a drawing of a perspective view of an interferential current pattern indicating the current intensity level and area of beat frequency formation.

A pulse generator 204 is connected to the input of the digital signal processor 202 and supplies a pulsed digital signal output 216 to the digital signal processor 202. The digital signal 216 is processed by the digital signal processor 202 to create a first circuit 218 and a second circuit 220 at the first and second pairs of surface electrodes 208,209; 308,309; and 408, respectively. Where the first and second circuits 218, 220 superimpose, the resultant beat frequency (which is preferably between 1 and 250 beats/second) will be the difference between the frequencies of the two circuits, and the amplitude will be additive and greater than either circuit alone (FIG. 3).

Modulating the outputs of the first and second circuits 218, 410, 220, 420 increases the area of the targeted stimulation (FIG. 4). The depth of modulation can vary from 0 to 100% and depends on the direction of the currents established by the first and second circuits 218, 418, 220, 420. When the first and second circuits 218, 418, 220, 420 intersect at 90°, the maximum resultant amplitude and the deepest level of modulation is half-way between the two circuits (45° diagonally). (See FIG. 3). The area of stimulation can be augmented by modulation of the amplitudes of the outputs of the two circuits.

FIG. 4 shows the stimulator 200, 400 positioned to stimulate the two pairs of electrodes 208,209; 308,309; and 408, at the predetermined peripheral surface stimulation sites 410. One pair of electrodes may be utilized if we are utilizing NMES or TENS outputs and it is deemed effective due to the condition, and predetermined with Neural Imaging studies.

In an alternative embodiment, as described above, the digital signal processor may be replaced with the FPGA. Whereas DSP processors typically have only eight dedicated multipliers at their disposal, a higher end FPGA device can offer up to 224 dedicated multipliers plus additional logic element-based multipliers as needed. That allows for complex digital signal processing applications such as finite impulse response filters, forward error correction, modulation-demodulation, encryption and applications such as utilized in the present invention.

It should be emphasized that the above-described embodiments of the present invention, particularly, any "preferred" embodiments, are merely possible examples of implementations, merely set forth for a clear understanding on the principles of the invention. Many variations and modifications may be made to the above-described embodiment(s) of the invention without departing substantially from the spirit and principles of the invention. All such modifications and variations are intended to be included herein within the scope of this disclosure and the present invention, and protected by the following claims.

We claim:

1. A method for electrical stimulation of a subject's brain for treatment of neural disorders, said method comprising:
    connecting a pulse generator to a digital signal processor and supplying digital signal pulses to said digital signal processor for producing an approximate sine wave current waveform which is further processed and output to first and second pairs of surface electrodes, wherein first and second circuits are created, respectively; and
    positioning said first and second pairs of surface electrodes at predetermined peripheral surface stimulation sites on the subject's skin surface based at least in part on a neural image.

2. The method according to claim 1, wherein said method further includes creating an interferential current with a base medium frequency of at least 1 KHz but no more than 100 KHz.

3. The method according to claim 2, wherein said method further includes creating the interferential current with a resultant beat frequency of no more than 250 Hz.

4. The method according to claim 1, wherein said method further includes positioning said first and second pairs of surface electrodes using positron emission tomography and neural imaging devices to locate said peripheral surface stimulation sites.

5. The method according to claim 1, wherein said method further includes varying said positioning of said first and second pairs of surface electrodes.

6. The method according to claim 1, wherein said method further includes applying said approximate sine wave current waveform to said peripheral surface stimulation sites for at least 30 minutes but no more than 60 minutes.

7. The method of claim 1, wherein said first and second pairs of surface electrodes are configured to provide transcutaneous stimulation.

8. The method of claim 1, wherein said first and second pairs of surface electrodes are configured to provide percutaneous stimulation.

9. A method for electrical stimulation of a subject's brain for treatment of neural disorders, said method comprising:
    connecting a pulse generator to a field-programmable gate array and supplying digital signal pulses to said field-programmable gate array for producing an approximate sine wave current waveform which is further processed and output to first and second pairs of surface electrodes, creating first and second circuits, respectively; and
    positioning said first and second pairs of surface electrodes at predetermined peripheral surface stimulation sites on the subject's skin surface based at least in part on a neural image.

10. The method according to claim 9, wherein said method further includes creating an interferential current with a base medium frequency of at least 1 KHz but no more than 100 KHz.

11. The method according to claim 10, wherein said method further includes creating the interferential current with a resultant beat frequency of no more than 250 Hz.

12. The method according to claim 9, wherein said method further includes positioning said first and second pairs of surface electrodes using positron emission tomography and neural imaging devices to locate said peripheral surface stimulation sites.

13. The method according to claim 9, wherein said method further includes varying said positioning of said first and second pairs of surface electrodes.

14. The method according to claim 9, wherein said method further includes applying said approximate sine wave current waveform to said peripheral surface stimulation sites for at least 10 minutes but no more than 180 minutes.

15. The method of claim 9, wherein said first and second pairs of surface electrodes are configured to provide transcutaneous stimulation.

16. The method of claim 9, wherein said first and second pairs of surface electrodes are configured to provide percutaneous stimulation.

17. A method for electrical stimulation of a subject's brain for tremor control, said method comprising:
    positioning at least two pairs of surface electrodes at predetermined peripheral surface stimulation sites on the subject's skin surface based at least in part on a neural image; and
    supplying electrical stimulation to said at least two pairs of surface electrodes.

18. The method according to claim 17, wherein said method further includes supplying electrical stimulation from the group consisting of TENS, neuro-muscular, ultrasound, interferential, PEMF, EMF and mechanical stimulation.

19. A method for electrical stimulation of a subject's brain for treatment of neural disorders, said method comprising:
    positioning at least one pair of surface electrodes at predetermined peripheral surface stimulation sites on the subject's skin surface based at least in part on a neural image; and
    connecting a pulse generator to said at least one pair of surface electrodes and generating an electrical current.

20. The method according to claim 19, wherein said method further includes creating a pulsatile current with a with a square wave output, an amplitude range from 0-150 mA and a phase duration range of 1-500 μsec.

21. The method according to claim 20, wherein said method further includes creating the pulsatile current with a frequency range from 1 pps to 2500 pps.

22. The method according to claim 19, wherein said method further includes positioning said at least one pair of surface electrodes using positron emission tomography and neural imaging devices to locate said peripheral surface stimulation sites.

23. The method according to claim 19, wherein said method further includes varying said positioning of said at least one pair of surface electrodes.

24. The method according to claim 19, wherein said method further includes applying said electrical current to said peripheral surface stimulation sites with a duty cycle from as little as 1 second to 120 minutes on with an off time as little as 1 second to as long as 120 minutes.

25. The method according to claim 19, wherein said method further includes applying said electrical current continuously without a duty cycle.

26. The method of claim 19, wherein said at least one pair of surface electrodes stimulates the subject's brain transcutaneously.

27. The method of claim 19, wherein said at least one pair of surface electrodes stimulates the subject's brain percutaneously.

28. A method for electrical stimulation of a subject's brain for treatment of neural disorders, said method comprising:

connecting a pulse generator to a digital signal processor and supplying digital signal pulses to said digital signal processor for producing an approximate sine wave current waveform which is further processed and output to first and second pairs of surface electrodes, wherein first and second circuits are created, respectively; and positioning said first and second pairs of surface electrodes at predetermined peripheral surface stimulation sites on the subject's skin surface, wherein said method further includes positioning said first and second pairs of surface electrodes using positron emission tomography and neural imaging devices to locate said peripheral surface stimulation sites.

29. A method for electrical stimulation of a subject's brain for treatment of neural disorders, said method comprising:

connecting a pulse generator to a field-programmable gate array and supplying digital signal pulses to said field-programmable gate array for producing an approximate sine wave current waveform which is further processed and output to first and second pairs of surface electrodes, creating first and second circuits, respectively; and positioning said first and second pairs of surface electrodes at predetermined peripheral surface stimulation sites on the subject's skin surface, wherein said method further includes positioning said first and second pairs of surface electrodes using positron emission tomography and neural imaging devices to locate said peripheral surface stimulation sites.

30. A method for electrical stimulation of a subject's brain for treatment of neural disorders, said method comprising:

positioning at least one pair of surface electrodes at predetermined peripheral surface stimulation sites on the subject's skin surface; and connecting a pulse generator to said at least one pair of surface electrodes and generating an electrical current, wherein said method further includes positioning said at least one pair of surface electrodes using positron emission tomography and neural imaging devices to locate said peripheral surface stimulation sites.

* * * * *